(12) United States Patent
Tinetti et al.

(10) Patent No.: US 8,362,051 B2
(45) Date of Patent: Jan. 29, 2013

(54) MOLD-RESISTANT WALLBOARD

(75) Inventors: Sheila M. Tinetti, Vernon Hills, IL (US); Paul Foley, Midland, MI (US); Li Wang, Arlington Heights, IL (US); Michael V. Enzien, Lisle, IL (US); Sanjay B. Bishnoi, Wilmette, IL (US)

(73) Assignee: Rohm and Haas Company, Philadelphia, PA (US)

( * ) Notice: Subject to any disclaimer, the term of this patent is extended or adjusted under 35 U.S.C. 154(b) by 568 days.

(21) Appl. No.: 12/523,875

(22) PCT Filed: Jan. 18, 2008

(86) PCT No.: PCT/US2008/051433
§ 371 (c)(1),
(2), (4) Date: Jul. 21, 2009

(87) PCT Pub. No.: WO2008/091794
PCT Pub. Date: Jul. 31, 2008

(65) Prior Publication Data
US 2010/0256204 A1    Oct. 7, 2010

Related U.S. Application Data

(60) Provisional application No. 60/897,670, filed on Jan. 26, 2007.

(51) Int. Cl.
| | |
|---|---|
| *A01N 43/80* | (2006.01) |
| *A01N 43/40* | (2006.01) |
| *A01N 43/52* | (2006.01) |
| *A01N 43/78* | (2006.01) |
| *A01N 33/18* | (2006.01) |
| *A01N 37/52* | (2006.01) |
| *A01N 41/10* | (2006.01) |
| *A01N 47/10* | (2006.01) |
| *A01N 55/02* | (2006.01) |
| *D21H 21/36* | (2006.01) |
| *B32B 13/08* | (2006.01) |

(52) U.S. Cl. ........ 514/372; 514/345; 514/365; 514/367; 514/395; 514/479; 514/491; 514/494; 514/525; 514/526; 514/634; 514/709; 514/736; 514/741; 424/411; 424/413; 424/414

(58) Field of Classification Search .......... 424/411, 424/413, 414; 514/372, 395, 479, 345, 365, 514/367, 491, 494, 525, 526, 634, 709, 736, 514/741; 106/780; 156/39
See application file for complete search history.

(56) References Cited

U.S. PATENT DOCUMENTS

| | | | |
|---|---|---|---|
| 4,105,431 A | 8/1978 | Lewis et al. | |
| 6,197,805 B1 * | 3/2001 | Smith | 514/388 |
| 6,680,127 B2 | 1/2004 | Capps | |
| 6,703,331 B1 | 3/2004 | Bruce et al. | |
| 6,767,647 B2 | 7/2004 | Swofford et al. | |
| 6,773,822 B2 | 8/2004 | Capps | |
| 2003/0035981 A1 | 2/2003 | Capps | |
| 2003/0234068 A1 | 12/2003 | Swofford et al. | |
| 2004/0005484 A1 | 1/2004 | Veeramasuneni et al. | |
| 2005/0003163 A1 | 1/2005 | Krishnan | |
| 2005/0153151 A1 | 7/2005 | Fay et al. | |
| 2006/0008496 A1 | 1/2006 | Kulkarni et al. | |
| 2006/0008513 A1 | 1/2006 | Holbert et al. | |
| 2006/0027948 A1 | 2/2006 | Grass et al. | |
| 2006/0035097 A1 * | 2/2006 | Batdorf | 428/507 |
| 2006/0105657 A1 | 5/2006 | Cline et al. | |
| 2006/0169431 A1 | 8/2006 | Marks et al. | |
| 2006/0171976 A1 | 8/2006 | Weir et al. | |
| 2010/0016394 A1 | 1/2010 | Enzien | |
| 2010/0041629 A1 * | 2/2010 | Giessler-Blank et al. | 514/65 |

FOREIGN PATENT DOCUMENTS

| | | | |
|---|---|---|---|
| EP | 375367 | * | 6/1990 |
| WO | 2006007044 | | 1/2006 |
| WO | 2006014426 | | 2/2006 |
| WO | 2006014446 | | 2/2006 |
| WO | 2006067390 | | 6/2006 |
| WO | 2007025734 | | 8/2007 |
| WO | 2008091794 | | 7/2008 |

OTHER PUBLICATIONS

Gorny et al., "Fungal Fragments as Indoor Air Biocontaminants", Applied and Environmental Microbiology, Jul. 2002, pp. 3522-3531, vol. 68, No. 7, American Society for Microbiology.
"Gypsum Board", Kirk-Othmer Encyclopedia of Chemical Technology, Second Edition, 1970, pp. 621-624.
Directory of Microbicides for the Protection of Materials, A Handbook; 2005; pp. 661-662; published by Springer.
Office Communication dated Oct. 12, 2011; U.S. Appl. No. 12/503,441.

* cited by examiner

*Primary Examiner* — John Pak
(74) *Attorney, Agent, or Firm* — Tifani M. Edwards

(57) ABSTRACT

Wallboard and facing paper that provides increased mold resistance at lower biocide loadings. The biocide is: (a) an n-alkyl isothiazolinone such as octylisothiazolinone (OIT), a monohalo and dihalo substituted n-alkylisothiazolinone such as chloromethylisothiazolinone (CMIT) or dichlorooctylisothiazolinone (DCOIT), 3-iodo-2-propynyl-butylcarbamate (IPBC), chlorothalonil, methylene-bis-thiocyanate, or mixtures of two or more thereof; or (b) carbendazim and a second biocide selected from 3-iodo-2-propynyl-butylcarbamate (IPBC), diiodomethyltolylsulfone (DIMTS), sodium pyrithione, octylisothiazolinone (OIT), dichlorooctylisothiazolinone (DCOIT), and chlorothalonil.

10 Claims, No Drawings

MOLD-RESISTANT WALLBOARD

CROSS-REFERENCE TO RELATED APPLICATIONS

This is a §371 application of PCT International Patent Application Number PCT/US2008/051433 filed Jan. 18, 2008, and claims priority to U.S. provisional patent application Ser. No. 60/897,670, filed Jan. 26, 2007, each of which is incorporated herein by reference in its entirety.

FIELD OF THE INVENTION

The invention relates to wallboard, wallboard facing paper, and methods of use, that provide mold resistance at lower loadings of biocide than in conventional mold-resistant wallboard.

BACKGROUND OF THE INVENTION

Fungal growth is a serious threat to human health, and the potential costs for remediation or replacement of contaminated building materials are astronomical. Fungal spores, released from surface growth, are well-recognized as allergens, and additional concerns have been raised due to toxic byproducts of at least one species. According to recent studies by Gorny et al. (Appl. Environ. Microbiol., July 2002, p. 3522-3531), occupant exposure to various health problems, including those referred to as "sick building syndrome," is increasing. Further concern is being raised by human allergic responses, similar to that observed with fungal spores, to fungal fragments that can be released at much lower humidity levels (as low as 20%).

Paper and paperboard used in those building materials have been observed as the sites for such fungal growth. Typical moisture in paper, paperboard, and building materials is sufficient to maintain growth. The cellulose of the paper and paperboard, along with the residual contaminants within the fiber web, offer a sufficient food source that is enhanced by other building product components such as starch binders.

Since fungi can grow in temperatures from as low as 40° F. to as high as 130° F., most indoor conditions, as well as a large segments of outdoor conditions, will easily allow their growth. Although efforts have been made to use careful construction practices and humidity control to limit fungal growth, fungi contamination problems have been observed in regions such as the Northeast U.S. where relative humidity rarely exceeds recommended maximums, and building materials were not exposed to the weather. Atmospheric fungal spores provide sufficient inoculation of fungi to the materials, and added moisture from condensation or water damage makes the threat of fungal contamination more likely.

Homeowners typically see fungal growth in closets, along baseboards and on bathroom walls; removal of installed panels may reveal hidden growth on the backside. Areas with even minor water damage or condensation are often heavily contaminated. Growth is visible as dark green or black spots that can grow to a complete covering of the affected area. Many after-market treatments, usually based on chlorine bleach, lighten the spots. Such treatments tend to damage the paint or coating after multiple treatments and do not prevent return of fungi.

Gypsum panels are used for drywall building products and are in heavy use for residential, educational, and commercial buildings. Gypsum panels are used primarily for interior wall and ceiling construction, and some specialty panels are used in exterior applications. Even though fungal contamination can come from the gypsum core, made of calcium sulfate hemihydrates, the primary location for fungal growth on gypsum panels is the facing paper that covers each side of the gypsum core. Once installed, gypsum panels can make treatment and/or remediation extremely difficult and expensive, as fungal contamination may be enclosed and inaccessible.

Current methods used to render gypsum board mold-resistant per industry metrics generally require the use of high levels of antimicrobial agents in the cellulose-based facing paper. Also, fixatives, such as cationic fixatives, are generally needed to enhance the efficacy of the antimicrobial when it is added to the wet-end of the paper-making process. In addition, antimicrobials sometimes also need to be added to the gypsum core to further enhance mold-resistance. The use of high antimicrobial loadings in gypsum board is commercially undesirable for a number of reasons, cost being the primary consideration. In addition, production difficulties often arise when attempting to use high levels of antimicrobials.

Thiabendazole, zinc pyrithione, and diiodomethyltolylsulfone (DIMTS) have been applied commercially in mold-resistant paper facers for use in gypsum board. Thiabendazole (TBZ) and zinc pyrithione (ZPT) have been replaced predominately by DIMTS and the technology described in US20060169431A1, which is incorporated herein by reference. Commercially practiced loadings for DIMTS-treated paper used for gypsum wallboard are generally on the order of 700-1000 ppm. Sodium pyrithione, a highly water-soluble antimicrobial, is sometimes used to treat the gypsum core of mold-resistant wallboard.

A continuing need exists for wallboard materials that provide enhanced mold resistance and that require lower biocide loadings.

BRIEF SUMMARY OF THE INVENTION

In one aspect, the invention provides a wallboard that is mold resistant. The wallboard comprises a gypsum core and wallboard facing paper on one or both faces of the core. The facing paper comprises a biocide that is:
   (a) an n-alkyl isothiazolinone such as octylisothiazolinone (Off), a monohalo or dihalo substituted n-alkylisothiazolinone such as chloromethylisothiazolinone (CMIT) or dichlorooctylisothiazolinone (DCOIT), 3-iodo-2-propynyl-butylcarbamate (IPBC), chlorothalonil, methylene-bis-thiocyanate, or mixtures of two or more thereof; or
   (b) carbendazim and a second biocide selected from 3-iodo-2-propynyl-butylcarbamate (IPBC), diiodomethyltolylsulfone (DIMTS), sodium pyrithione, octylisothiazolinone (Off), dichlorooctylisothiazolinone (DCOIT), and chlorothalonil.

In a further aspect, the invention provides multi-ply wallboard facing paper that comprises a biocide that is:
   (a) an n-alkyl isothiazolinone, a monohalo or dihalo substituted n-alkylisothiazolinone, IPBC, chlorothalonil, methylene-bis-thiocyanate, or mixtures of two or more thereof; or
   (b) carbendazim and a second biocide selected from 3-iodo-2-propynyl-butylcarbamate (IPBC), diiodomethyltolylsulfone (DIMTS), sodium pyrithione, octylisothiazolinone (Off), dichlorooctylisothiazolinone (DCOIT), and chlorothalonil.

In a further aspect, the invention provides a method for inhibiting the growth of mold on wallboard, by providing the wallboard with facing paper as described herein.

DETAILED DESCRIPTION OF THE INVENTION

The invention provides a mold resistant facing paper for use in wallboard, mold resistant wallboard, and methods of use thereof for the inhibition of mold in a building. The wallboard of the invention comprises: a gypsum core and facing paper on one or more of its faces.

To provide improved mold resistance, the facing paper of the invention contains a biocide selected from an n-alkyl isothiazolinone such as OIT, a monohalo or dihalo substituted n-alkylisothiazolinones such as CMIT or DCOIT, IPBC, chlorothalonil, methylene-bis-thiocyanate, and mixtures of two or more thereof.

Preferably, the loading level of the biocide in the facing paper is up to about 3000 ppm, preferably up to about 1000 ppm, more preferably up to about 750 ppm, even more preferably, up to about 500 ppm, and more preferably up to about 300 ppm. Further, the biocide concentration is preferably at least about 25 ppm, more preferably at least about 50 ppm, and even more preferably, at least about 75 ppm.

Additional biocides may be included in or on the facing paper, such as, but not limited to, diiodomethyl-p-tolylsulfone (DIMTS), zinc pyrithione, thiabendazole, o-phenylphenol (OPP) and its corresponding salts, bromonitrostyrene (BNS), 2-(thiocyanomethylthio) benzothiazole (TCMTB), sodium pyrithione, carbendazim, dodecylguanidine hydrochloride, bis-(dimethyldithiocarbamato)-zinc (ziram), bis (dimethylthiocarbamoyl)disulfide (thiram), or mixtures of two or more thereof. The facing paper may contain other optional components, such as additives that increase the moisture resistance of the facing paper including wax, silicones, or fluorochemicals, retention aids, flocculants, fixatives, sizing agents, binders, fillers, and thickeners.

A particularly preferred n-alkyl isothiazolinone for use in the facing paper is octylisothiazolinone (OIT). The inventors have discovered that OIT, when incorporated into gypsum wallboard facing paper, is surprisingly effective at inhibiting the growth of mold at very low concentrations when compared to other biocides currently used in this field and wallboard facing paper that does not contain biocide.

The OIT is present in the facing paper at a preferred loading of up to about 1000 ppm, more preferably up to about 750 ppm, even more preferably, up to about 500 ppm, and more preferably up to about 300 ppm. Further, the OIT concentration is preferably at least about 25 ppm, more preferably at least about 50 ppm, and even more preferably, at least about 100 ppm. In further preferred embodiments, the loading of OIT in the facing paper is between about 25 and 1000 ppm, more preferably between about 50 and 500 ppm, and even more preferably, between about 100 and 300 ppm. Most preferably, the concentration is between about 100 ppm and about 200 ppm.

In a further preferred embodiment, the biocide is a mixture of OIT and DCOIT. The OIT/DCOIT mixture is present in the facing paper at a preferred total loading of up to about 1000 ppm, more preferably up to about 750 ppm, even more preferably, up to about 500 ppm, and more preferably up to about 300 ppm. Further, the OIT/DCOIT concentration is preferably at least about 25 ppm, more preferably at least about 50 ppm, and even more preferably, at least about 100 ppm. In further preferred embodiments, the loading of OIT/DCOIT in the facing paper is between about 25 and 1000 ppm, more preferably between about 50 and 500 ppm, and even more preferably, between about 100 and 300 ppm. Most preferably, the concentration is between about 100 ppm and about 200 ppm.

In another preferred embodiment, the biocide is IPBC. The IPBC is present in the facing paper at a preferred loading of up to about 1000 ppm, more preferably up to about 750 ppm, even more preferably, up to about 500 ppm, and more preferably up to about 300 ppm, and further preferably up to about 100 ppm. Further, the IPBC concentration is preferably at least about 25 ppm, and more preferably at least about 50 ppm. In further preferred embodiments, the loading of IPBC in the facing paper is between about 25 and 1000 ppm, more preferably between about 50 and 500 ppm, and even more preferably, between about 50 and 200 ppm. In an alternative of this IPBC embodiment, the facing paper contains IPBC, preferably at the above loadings, but is substantially free of other biocides. By "substantially free" is meant that the facing paper contains no more than 100 ppm, preferably no more than 75 ppm, more preferably no more than 50 ppm, and even more preferably no more than 25 ppm of biocides other than IPBC. Most preferably, the paper contains less than 5 ppm, or is free of, biocides other than IPBC.

In another preferred embodiment, the biocide is a mixture of IPBC and a second biocide selected from carbendazim (BCM), ziram, and thiram. The mixture is present in the facing paper at a preferred total loading of up to about 1000 ppm, more preferably up to about 750 ppm, even more preferably, up to about 500 ppm, and more preferably up to about 300 ppm. Further, the IPBC/second biocide concentration is preferably at least about 25 ppm, more preferably at least about 50 ppm, and even more preferably, at least about 100 ppm. In further preferred embodiments, the loading of IPBC/second biocide in the facing paper is between about 25 and 1000 ppm, more preferably between about 50 and 500 ppm, and even more preferably, between about 100 and 300 ppm. Most preferably, the concentration is between about 100 ppm and about 200 ppm. The ratio of IPBC to second biocide is 3:1 to 1:3 most preferably 1:3. In this embodiment, a particularly preferred second biocide is carbendazim.

In a further preferred embodiment, the biocide is a mixture of carbendazim and a second biocide selected from the group consisting of DIMTS, sodium pyrithione, OIT, DCOIT, and chlorothalonil. The mixture is present in the facing paper at a preferred total loading of up to about 1000 ppm, more preferably up to about 750 ppm, even more preferably, up to about 500 ppm, and more preferably up to about 300 ppm. Further, the carbendazim/second biocide concentration is preferably at least about 25 ppm, more preferably at least about 50 ppm, and even more preferably, at least about 100 ppm. In further preferred embodiments, the loading of carbendazim/second biocide in the facing paper is between about 25 and 1000 ppm, more preferably between about 50 and 500 ppm, and even more preferably, between about 100 and 300 ppm. Most preferably, the concentration is between about 100 ppm and about 200 ppm. The ratio of carbendazim to second biocide is 3:1 to 1:3 most preferably 1:3.

The wall board facing paper used in the invention is typically a multi-ply (e.g., 2 to 9 layers) cellulose based material manufactured from re-pulped newspapers or other recycled products such as corrugated cardboard or office paper. The basis weight of the paper is generally 36-60 lbs/1000 ft$^2$, preferably 40-50 lbs/1000 ft$^2$. For multi-layered facing paper, the biocide can be included in or on any layer. Preferably the biocide is included in or on the outer 1 to 3 layers of the multi-layered facing paper.

Although multi-layered paper is preferred, the invention is also applicable to single-ply cellulose based paper. In addition, although for clarity the invention is discussed in terms of gypsum wallboard, it is suitable for use in other cellulose based building materials requiring mold resistance, such as facing paper for insulation, fiberglass-cellulose coverings, ceiling tile, backing for vinyl flooring, and air filters.

The biocide may be incorporated into the paper or it may be applied to one or both surfaces of the paper. The biocide may be added during any stage of the paper manufacturing process, including at the "wet-end" (e.g. thick stock, thin stock, machine chest, head box), or at the "dry-end" after the paper is formed such as by dipping, spraying, or other surface coating techniques (e.g. size press, calender stack, water box, spray bar, off-machine coater). The biocide can alternatively be applied to the surface of the paper during the manufacture of the wallboard as the paper is unrolled, after the paper facer is in contact with the gypsum slurry, after the gypsum slurry has set and sheets have been formed, and/or after the sheets have been further cut into standard sizes. Furthermore, the biocide may be applied onto the inner surface, the outer surface, or both of the front and/or back paper facings.

Where the biocide is IPBC, surface treatment is preferred and may be accomplished by the various techniques described above.

Where the biocide contains OIT or DCOIT, it is preferably incorporated into the paper. For this embodiment, The preferred addition point is at the machine chest in the wet end. Because of the low concentration of biocide provided by the invention, adding the biocide during wet end processing does not significantly alter the slurry composition and the normal paper production process, and therefore does not require expensive disruption or alteration of the paper manufacturing equipment.

A major ingredient of gypsum wallboard core is calcium sulfate hemihydrate, commonly referred to as "calcined gypsum," "stucco," or "plaster of Paris." Stucco has a number of desirable physical properties including its fire resistance, thermal and hydrometric dimensional stability, compressive strength, and neutral pH. Generally, wallboard is produced by enclosing a core of an aqueous slurry containing calcined gypsum and other materials between two large sheets of wallboard facing paper. After the gypsum slurry has set (i.e., reacted with the water present in the aqueous slurry) and dried, the formed sheet is cut into standard sizes. Methods for the production of gypsum wallboard generally are described, for example, in Kirk-Othmer Encyclopedia of Chemical Technology, Second Edition, 1970, Vol. 21, pages 621-24, the disclosure of which is incorporated herein by reference.

The gypsum core may contain various additional ingredients, including accelerators (such as potassium sulfate) for controlling the set time of the stucco, antidessicants (such as starch) to prevent the dehydration of calcium sulfate dihydrate crystals formed during setting of the core composition, additional lightweight aggregates (e.g., expanded perlite or vermiculite), and additives that increase the moisture resistance of the finished core (such as wax, silicones, or fluorochemicals). The core may also contain biocides for further retarding fungal growth, such as, but not limited to, sodium pyrithione, diiodomethyl-p-tolylsulfone (DIMTS), zinc pyrithione, thiabendazole, IPBC, n-alkyl isothiazolinones such as octylisothiazolinone (OIT), monohalo and dihalo substituted n-alkylisothiazolinones such chloromethylisothiazolinone (CMIT) and dichlorooctylisothiazolinone (DCOIT), methylene-bis-thiocyanate, dodecylguanidine hydrochloride, phenolics such as o-phenylphenol (OPP) and its corresponding salts, bromonitrostyrene (BNS), 2-(thiocyanomethylthio) benzothiazole (TCMTB), sodium pyrithione, carbendazim, chlorothalonil, bis-(dimethyldithiocarbamato)-zinc (ziram), bis(dimethylthiocarbamoyl)disulfide (thiram), or mixtures of two or more thereof.

In a further aspect, the invention provides a method for inhibiting mold growth in wallboard, the method comprising providing the facing paper of the wallboard with biocides as described above.

The following examples are presented to illustrate the invention and are not to be interpreted as limiting its scope.

EXAMPLES

Example 1

OIT Compared to DIMTS

The biocides can be evaluated in the following examples by adding to a 0.4 wt % pulp slurry in water (100% recycle) typically used for gypsum wallboard facing paper. The slurry is filtered through a screen to drain the water from the stock and the resulting paper mat is blotted, couched, and dried to form a paper sheet with a basis weight of approximately 40 lb/1000 ft2. Three sheets per condition are prepared. High Performance Liquid Chromatography (HPLC) is used to determine the amount of biocide present in each sheet. The paper sheets are evaluated for fungal growth via ASTM 3273, currently the industry standard for mold-resistant wallboard, as well as the standard TAPPI T-487 fungal efficacy test.

The values in Tables 1 and 2 below represent data from samples made substantially according to the preceding protocol. The average concentration of active biocide in the paper and the average test rating based on three paper sheets are shown. Based on tables 1 and 2, approximately 4-4.5 times more DIMTS active was needed in the paper sheet than OIT before no mold growth was observed throughout the entire testing period.

For ASTM 3273, a 4-week test, the following rating scale applies:
   0—100% mold coverage
   1—90% mold coverage
   2—80% mold coverage
   3—70% mold coverage
   4—60% mold coverage
   5—50% mold coverage
   6—40% mold coverage
   7—30% mold coverage
   8—20% mold coverage
   9—10% mold coverage
   10—no mold growth For TAPPI T-487, a 3-week test, the following rating scale applies:
   0—no mold growth
   1—25% mold coverage
   2—50% mold coverage
   3—75% mold coverage
   4—100% mold coverage

TABLE 1

ASTM 3273 Data

| Biocide | Concentration (ppm) | Week 1 | Week 2 | Week 3 | Week 4 |
|---|---|---|---|---|---|
| None | NA | 0 | 0 | 0 | 0 |
| OIT | 113 | 10 | 10 | 10 | 10 |
| OIT | 174 | 10 | 10 | 10 | 10 |
| OIT | 283 | 10 | 10 | 10 | 10 |
| DIMTS | 370 | 10 | 8 | 0 | 0 |
| DIMTS | 660 | 10 | 8 | 7 | 6 |
| DIMTS | 1272 | 10 | 10 | 10 | 10 |

TABLE 2

TAPPI T-487 Data

| Biocide | Concentration (ppm) | Week 1 | Week 2 | Week 3 |
|---|---|---|---|---|
| None | NA | 4 | 4 | 4 |
| OIT | 181 | 0 | 0 | 0 |
| OIT | 309 | 0 | 0 | 0 |
| OIT | 492 | 0 | 0 | 0 |

TABLE 2-continued

TAPPI T-487 Data

| Biocide | Concentration (ppm) | Week 1 | Week 2 | Week 3 |
|---|---|---|---|---|
| DIMTS | 386 | 0 | 2 | 3 |
| DIMTS | 553 | 0 | 2 | 3 |
| DIMTS | 855 | 0 | 0 | 0 |

Example 2

IPBC Compared With DIMTS, ZPT, and TBZ

This example shows the effectiveness of IPBC at inhibiting mold growth as compared to DIMTS, ZPT, and TBZ. The papers of this example were prepared via surface treatment. The values in Table 3 below represent the average concentration of active biocide in the paper and the average TAPPI T-487 test rating based on three paper sheets. The TAPPI test rating scale is the same as used in Example 1. Based on the data in Table 3, IPBC is more effective at controlling mold growth at lower dosages than DIMTS, ZPT, and TBZ.

The TAPPI test rating scale in the following table is the same as used in Example 1.

TABLE 3

Surface Treatment of Paper with IPBC, DIMTS, ZPT, and TBZ (TAPPI T-487 test)

| Biocide | Concentration (ppm) | Week 1 | Week 2 | Week 3 |
|---|---|---|---|---|
| None | | 4 | 4 | 4 |
| IPBC | 6768 | 0 | 0 | 0 |
| IPBC | 688 | 0 | 0 | 0 |
| IPBC | 70 | 0 | 0 | 0 |
| DIMTS | 5389 | 0 | 0 | 0 |
| DIMTS | 563 | 0 | 0 | 0 |
| DIMTS | 43 | 2 | 4 | 4 |
| ZPT | 5408 | 0 | 0 | 0 |
| ZPT | 486 | 1 | 4 | 4 |
| ZPT | 60 | 4 | 4 | 4 |
| TBZ | 4107 | 0 | 0 | 0 |
| TBZ | 229 | 2 | 4 | 4 |
| TBZ | 31 | 4 | 4 | 4 |

Example 3

Carbendazim/IPBC Blend Compared to DIMTS

This example shows the efficacy of a 3:1 carbendazim (BCM)/IPBC blend (Polyphase 678) when incorporated into a paper during formation of the paper. Results are compared with paper hand sheets incorporating DIMTS in the same manner, as well as handsheets with no biocide added. Handsheets are formed using a commercial handsheet mold which makes sheets 8×8 inches in area. The weights of the handsheets are 11-12 lbs/1000 ft$^2$ representing the typical basis weight of just the liner (outer facing plys) of the multi-ply wallboard paper. The 3:1 carbendazim/IPBC blend is added to the paper slurry (0.7 wt %) prior to forming the handsheets. Recycled news print paper is used as the source of fiber for handsheets. High Performance Liquid Chromatography (HPLC) is used to determine the amount of biocide present in each sheet, however, this method is not capable of detecting the levels of IPBC in the handsheets, therefore only carbendazim values are reported in Table 4 as weight of active (mg) per kg of paper. The handsheets are evaluated for fungal resistance using ASTM G21 over a two-week test period. A and B represent replicate analyses of same handsheet in Table 4. The data suggests that a Carbendazim/IPBC blend is effective at controlling fungal growth at concentrations lower than that needed for DIMTS.

TABLE 4

ASTM-G21 Fungal Resistant Test Method on paper handsheets treated with Carbendazim/IPBC versus DIMTS.

| Treatment | Active Concentration* (ppm) | Mold Resistance Rating | | | |
|---|---|---|---|---|---|
| | | Week 1 | | Week 2 | |
| | | A | B | A | B |
| DIMTS | 281 | 1 | 1 | 4 | 4 |
| DIMTS | 297 | 1 | 1 | 4 | 4 |
| DIMTS | 354 | 0 | 0 | 1 | 1 |
| DIMTS | 732 | 0 | 0 | 0 | 0 |
| DIMTS | 748 | 0 | 0 | 0 | 0 |
| 3:1 BCM/IPBC | 24 | 4 | 4 | 4 | 4 |
| 3:1 BCM/IPBC | 31 | 4 | 4 | 4 | 4 |
| 3:1 BCM/IPBC | 52 | 3 | 2 | 4 | 4 |
| 3:1 BCM/IPBC | 93 | 1 | 0 | 4 | 1 |
| 3:1 BCM/IPBC | 116 | 0 | 0 | 0 | 1 |
| 3:1 BCM/IPBC | 110 | 0 | 0 | 0 | 0 |

*Concentration reported for the BCM/IPBC-treated sheets is for carbendazim

Mold Resistance Rating Scale:

| Observed growth on samples | Rating |
|---|---|
| None | 0 |
| Traces of growth (<10%) | 1 |
| Light growth (10-30%) | 2 |
| Medium growth (30-60%) | 3 |
| Heavy growth (60-complete coverage) | 4 |

The invention has been described with reference to various specific and preferred embodiments and techniques. However, it should be understood that many variations and modifications may be made while remaining within the spirit and scope of the invention.

What is claimed is:

1. A wallboard comprising:
   a gypsum core having a first face and a second face; and
   facing paper substantially covering the first face, the second face, or both the first face and the second face of the gypsum core,
   wherein the facing paper comprises a biocide that is octylisothiazolinone at a loading of between 50 and 500 ppm.

2. The wallboard of claim 1 wherein the biocide is distributed through the facing paper.

3. The wallboard of claim 1 wherein the gypsum core comprises a biocide selected from the group consisting of: diiodomethyl-p-tolylsulfone (DIMTS), zinc pyrithione, thiabendazole, IPBC, n-alkyl isothiazolinones, monohalo and dihalo substituted n-alkylisothiazolinones, methylene-bis-thiocyanate, dodecylguanidine hydrochloride, phenolics, bromonitrostyrene (BNS), 2-(thiocyanomethylthio) benzothiazole (TCMTB), sodium pyrithione, carbendazim, chlorothalonil, bis-(dimethyldithiocarbamato)-zinc (ziram), bis (dimethylthiocarbamoyl)disulfide (thiram), and mixtures of two or more thereof.

4. The wallboard of claim 3, wherein the n-alkyl isothiazolinone is octylisothiazolinone (OIT), the monohalo and dihalo substituted n-alkylisothiazolinones are chloromethylisothiazolinone (CMIT) and dichlorooctylisothiazolinone (DCOIT), and/or the phenolics are o-phenylphenol (OPP) and its corresponding salts.

5. The wallboard of claim 1 wherein the facing paper comprises an additional biocide selected from the group consisting of: diiodomethyl-p-tolylsulfone (DIMTS), zinc pyrithione, thiabendazole, phenolics or salts thereof, bromonitrostyrene (BNS), 2-(thiocyanomethylthio) benzothiazole (TCMTB), sodium pyrithione, carbendazim, dodecylguanadine hydrochloride, bis-(dimethyldithiocarbamato)-zinc (ziram), bis(dimethylthiocarbamoyl)disulfide (thiram), and mixtures of two or more thereof.

6. The wallboard of claim 1 wherein the facing paper is single ply cellulose based paper.

7. The wallboard of claim 1 wherein the facing paper is multi-layered cellulose based paper having between 2 and about 9 layers.

8. The wallboard of claim 7 wherein the biocide is in or on the outer 1 to 3 layers of the multi-layered facing paper.

9. Facing paper for use with wallboard, the facing paper comprising a biocide that is
    octylisothiazolinone at a loading of between 50 and 500 ppm, wherein the facing paper is multi-layered cellulose based paper.

10. A method for inhibiting the growth of mold in building materials that contain facing paper, the method comprising including in or on the paper a biocide that is
    octylisothiazolinone at a loading of between 50 and 500 ppm.

* * * * *

UNITED STATES PATENT AND TRADEMARK OFFICE
CERTIFICATE OF CORRECTION

PATENT NO.         : 8,362,051 B2
APPLICATION NO.    : 12/523875
DATED              : January 29, 2013
INVENTOR(S)        : Sheila M. Tinetti et al.

It is certified that error appears in the above-identified patent and that said Letters Patent is hereby corrected as shown below:

Title Page

No. 73 - "Rohm and Haas Company" should read -- Dow Global Technologies LLC --

Signed and Sealed this
Ninth Day of April, 2013

Teresa Stanek Rea
*Acting Director of the United States Patent and Trademark Office*